United States Patent [19]
Hayhurst

[11] Patent Number: 5,100,415
[45] Date of Patent: Mar. 31, 1992

[54] KNOTTING INSTRUMENT

[76] Inventor: John O. Hayhurst, 14751 SE. Wanda Dr., Milwaukie, Oreg. 97267

[21] Appl. No.: 594,102

[22] Filed: Oct. 5, 1990

Related U.S. Application Data

[63] Continuation of Ser. No. 461,621, Jan. 8, 1990, Pat. No. 4,961,741.

[51] Int. Cl.⁵ .................... A61B 17/00; D03J 3/00
[52] U.S. Cl. ........................ 606/139; 289/17
[58] Field of Search ........... 606/139, 144, 148, 170; 289/1.5, 2, 17; 30/161, 167; 81/441

[56] References Cited

U.S. PATENT DOCUMENTS 2,610,631  9/1952  Calicchio ...................... 289/17
4,403,797  9/1983  Ragland ........................ 289/17

FOREIGN PATENT DOCUMENTS 0552077  3/1977  U.S.S.R. ....................... 606/144

Primary Examiner—Stephen C. Pellegrino
Assistant Examiner—Gary Jackson
Attorney, Agent, or Firm—Klarquist, Sparkman, Campbell, Leigh & Whinston

[57] ABSTRACT

A knotting instrument (20) having a leading member (22) and a trailing member (24) for forming a double knot. The leading member (22) functions to slide a first knot (26) that is formed in the sutures (30, 32) against the surface (34) of tissue (40). A finger (60) is formed in the leading member (24) to hold the first knot (26) against the tissue surface (34) as a second knot (28) is moved by the trailing member (24) against the first knot (26). The leading member (22) is configured to part as the trailing member (24) moves the second knot (28) against the first knot (26).

3 Claims, 3 Drawing Sheets

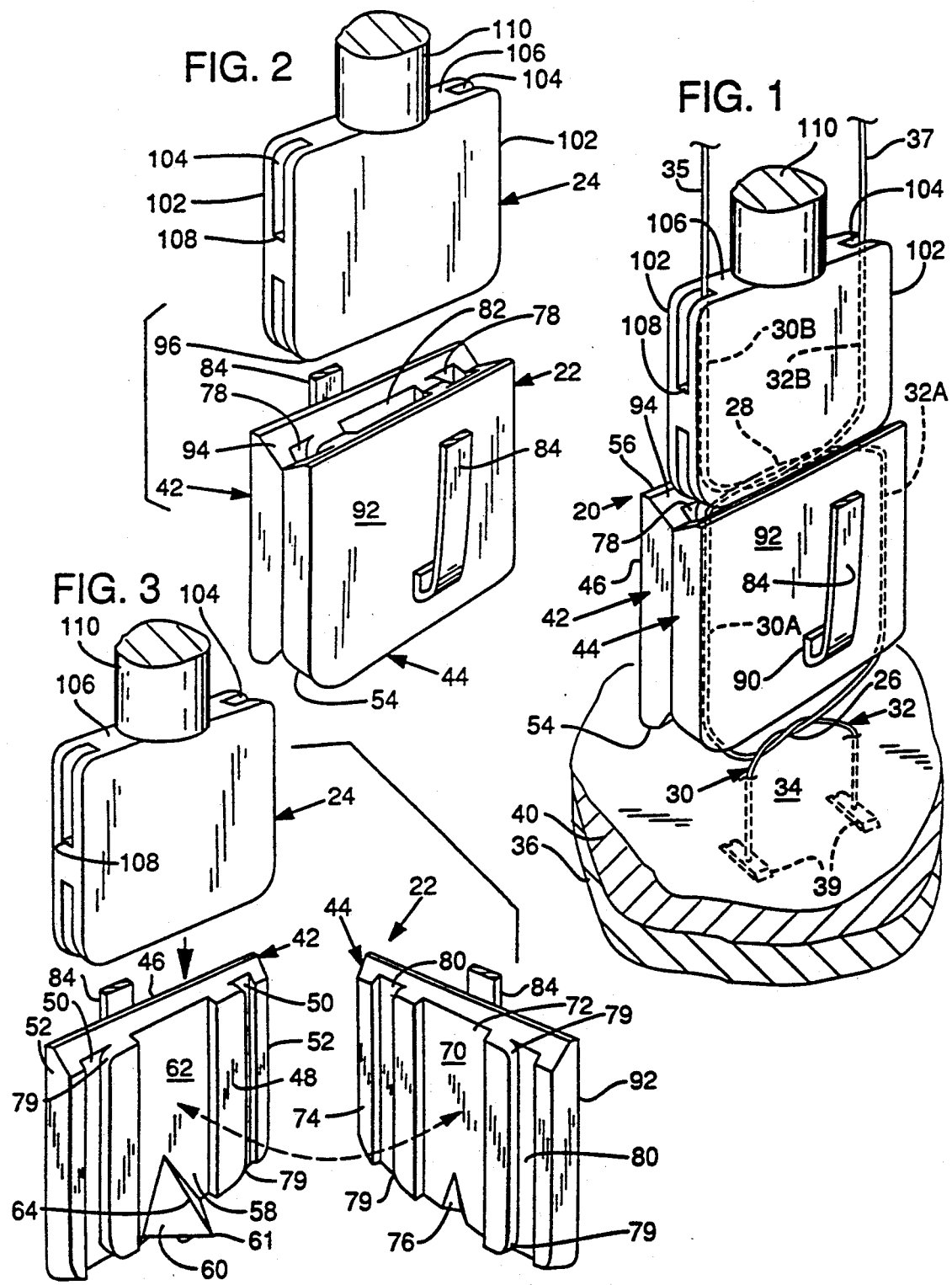

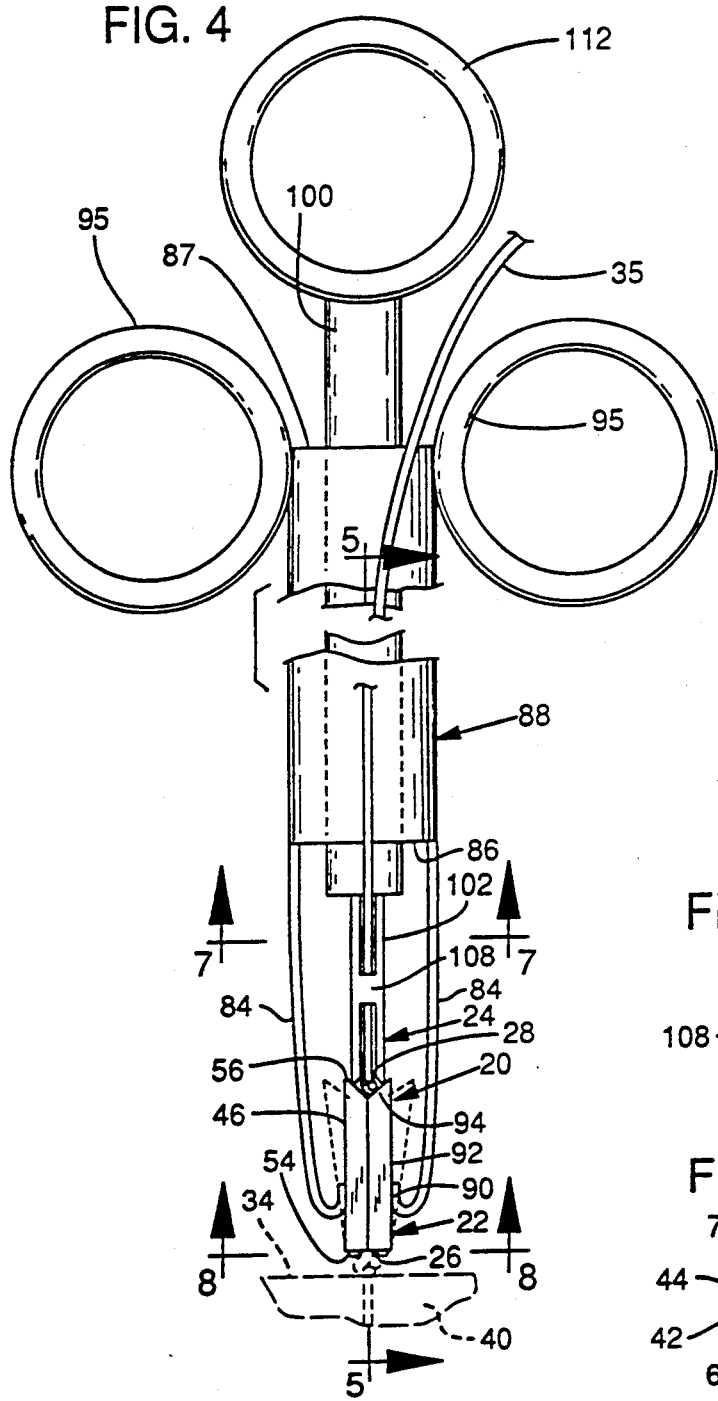
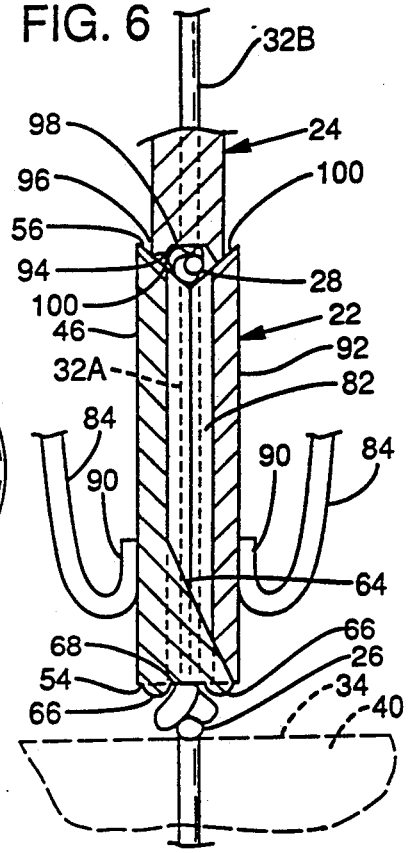
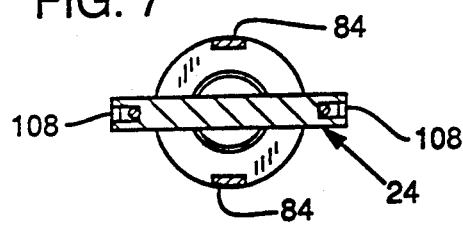
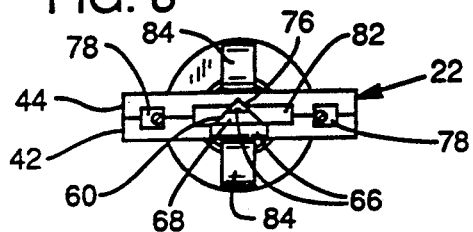

KNOTTING INSTRUMENT

CROSS-REFERENCE TO RELATED APPLICATION

This is a continuation of application Ser. No. 07/461,621, filed Jan. 8, 1990, U.S. Pat. No. 4,961,741.

TECHNICAL FIELD

This invention pertains to suturing, and particularly to instruments and methods for knotting sutures.

BACKGROUND INFORMATION

Suturing is a well-known technique for reuniting the edges of a wound or incision. In many instances, the wound or incision is exposed to an extent that is sufficient to permit a surgeon to tie the suture ends into a double knot. Recent advances in surgical procedures, particularly in the area of arthroscopic surgery, have, however, presented surgeons with problems that require new approaches to suturing.

Arthroscopic surgery generally involves the use of an arthroscope for examining the interior of an injured joint, such as a knee or shoulder. The arthroscope is inserted through a small incision made in the skin. The surgeon is able to view the joint interior through the arthroscope. Surgical instruments are inserted through other small incisions. The surgeon, guided by the arthroscope, is able to perform the surgery without the need to expose the joint with a large incision.

Typically, the arthroscopic surgical procedure employs sutures for reuniting torn tissues or cartilage or for anchoring cartilage to bone. In either case, a problem associated with arthroscopic surgical techniques arises because the surgeon is unable to place his fingers inside the joint, adjacent to the sutured tissue, for the purpose of tying the suture ends into a tight double knot.

An elongated, loop-ended, instrument has been used in the past as an aid in tying suture ends into a double knot near tissue that is inaccessible to the surgeon's fingers. With this technique, the suture ends that extend outside of the incision are tied into a single knot. One of the suture ends that extends from the single knot is then threaded through the small loop formed in the end of the instrument. The instrument is passed through the incision, loop end first, while the surgeon holds the suture ends. As the loop is moved toward the tissue, the knot slides along the sutures. The knot is moved adjacent to the surface of the tissue, and the instrument is then withdrawn from the incision and slid off the suture end. A second knot is then tied in the suture ends, and the loop is used in a manner as just described to slide the second knot toward the first knot that is adjacent to the tissue. With the second knot held by the instrument near the first knot, the surgeon then tightens the suture ends to form a double knot at the tissue.

A problem with the instrument just described is that in the course of sliding the second knot toward the first knot, the tension on the suture ends causes the first knot to lift off the tissue so that the resultant double knot will not be formed close to the tissue. Accordingly, the suturing will be undesirably loose.

SUMMARY OF THE INVENTION

This invention is directed to a knotting instrument that is configured for delivering a first suture knot to a location where a double knot is to be formed and for securing the first knot tightly against the tissue as a second knot is moved against the first knot to form the double knot.

The invention includes a leading member that is configured for receiving suture segments that extend from a first knot in the sutures. The segments are received in a manner that permits the first knot to be slid into contact with the tissue at a location on the tissue where the double knot is to be formed. The suture segments pass through the leading member. A second knot is formed in the suture segments that extend from the leading member. The suture segments that extend from the second knot pass through a trailing member. The trailing member is constructed to permit the second knot to be slid along the sutures toward the first knot.

The knotting instrument of the present invention is configured so that the leading member opens to permit the trailing member to pass through it for the purpose of moving the second knot firmly against the first knot. Moreover, a finger-type mechanism is formed in the leading member to secure the first knot in position adjacent to the tissue as the second knot is slid against the first knot.

As another aspect of this invention, the knotting instrument is constructed so that the suture segments received in the leading member and in the trailing member are spaced apart a distance sufficient to permit the knots to be easily slid along the sutures until the knots reach the location where the double knot is to be formed.

As another aspect of this invention, a mechanism is provided for manipulating the leading and trailing members for use with an arthroscopic surgical procedure.

BRIEF DESCRIPTION OF THE DRAWINGS

FIG. 1 is a pictorial view of the primary components of a knotting instrument formed in accordance with the present invention showing a typical application of the instrument.

FIG. 2 is another pictorial view of the primary components of the knotting instrument.

FIG. 3 is a partly exploded pictorial view of the primary components of the knotting instrument.

FIG. 4 is a side elevation view of the knotting instrument showing a preferred mechanism for manipulating the instrument.

FIG. 6 is a sectional view taken along line 6—6 of FIG. 5.

FIG. 7 is a sectional view taken along line 7—7 of FIG. 4.

FIG. 8 is a bottom view taken along line 8—8 of FIG. 4.

DETAILED DESCRIPTION OF THE PREFERRED EMBODIMENT

Figure 5:
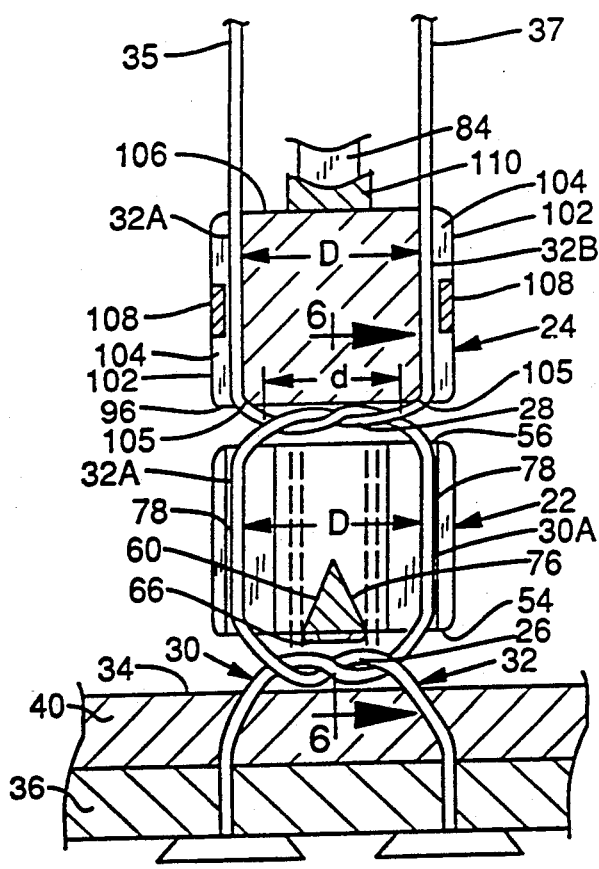
FIG. 5 is a sectional view taken along line 5—5 of FIG. 4.

Referring to FIGS. 1-9, the knotting instrument 20 of the present invention includes a leading member 22 and a trailing member 24 that are configured to guide a pair of suture knots 26, 28 against a tissue surface 34 so that the free ends 35, 37 of the sutures 30, 32 can be pulled to tighten the knots 26, 28 against the tissue surface 34.

Preferably, the instrument 20 is sized to pass through a small-diameter canula that extends through an incision in a joint. Such a canula is typically used in conjunction with an arthroscopic surgical procedure. It will be appreciated, however, that the present invention will be applicable to numerous other suturing applications where it is desirable to form a suture into a tight double knot close to a particular location.

In the preferred application of the present invention, the sutures 30, 32 may be anchored in bone or underlying tissue 36 by any suitable means, such as the depicted anchoring devices 39. The sutures 30, 32 pass through damaged or overlying tissue 40, such as cartilage, that is to be secured to the underlying tissue 36. Accordingly, it is necessary to form a double knot at the surface 34 of the overlying tissue 40 so that the sutures 30, 32 firmly secure the overlying tissue 40 to the underlying tissue 36.

The leading member 22 includes a first guide plate 42 and a second guide plate 44 normally held together to function as a single component. The first guide plate 42 includes a flat outer surface 46 and an inner surface 48 that is shaped to define grooves through which suture segments pass. More particularly, an outer groove 50 is formed to extend near each vertical side 52 of the first guide plate 42 from the bottom 54 of the leading member 22 to the top 56 of the leading member. The guide grooves 50 are shown as rectangular in cross section, although other cross-sectional shapes will suffice.

A single central groove 58 is formed in the inner surface 48 of the first guide plate 42. A pyramid-shaped finger 60 protrudes from the base surface 62 of the central groove 58 at the bottom 54 of the leading member 22. The finger 60 is shaped with an upper edge 64 that is inclined downwardly and outwardly from the base surface 62 of the central groove 58. The triangular shaped underside of the finger 60 is generally flat, except for a pair of spaced-apart ridges 66 that protrude downwardly therefrom to define a guide space 68 between the ridges 66 (FIGS. 6, 8). The significance of the guide space 68 is described more fully below.

The second guide plate 44 is substantially the mirror image of the first guide plate 42, except that instead of a protruding finger, a notch 76 is formed in the inner surface 74 of the second guide plate 44. Specifically, the notch 76 extends into the base surface 70 of the central groove 72 formed in the inner surface 74 of the second guide plate 44. The notch 76 is shaped to receive the tip 61 of the finger 60 when the inner surfaces 48, 74 of the first and second guide plates 42, 44 are brought together into a "closed" position of the leading member 22.

The juxtaposition of the first guide plate 42 and the second guide plate 44 that occurs when the leading member 22 is closed has the effect of defining outer passages 78 in the leading member. More particularly, the outer passages 78 result from the combination of the outer grooves 50 in the first guide plate 42 and the outer grooves 80 in the second guide plate 44. Moreover, the central grooves 58, 72 in the first and second guide plates 42, 44 form a central passage 82 from the top 56 to the bottom 54 of the leading member 22 (FIG. 2). The central passage 82 is interrupted near the bottom 54 of the leading member 22 by the portion of the finger 60 that extends across the central passage 82 when the leading member is in the closed position (FIG. 6).

The first guide plate 42 and second guide plate 44 are shaped to define a V-shaped groove 94 extending across the top 56 of the leading member 22 (FIG. 6). The significance of the V-shaped groove 94 is discussed more fully below.

The first guide plate 42 and second guide plate 44 are normally held together by mechanisms operable by the surgeon for parting the plates 42, 44 at the appropriate time as described more fully below. In the embodiment shown in the figures, the first guide plate 42 and second guide plate 44 are discrete members normally held together by springs 84. The springs 84 are preferably two thin strips of resilient material that extend from an inner end 86 of a tubular positioning member 88 that is used for placing the leading member 22 near the location where the sutures 30, 32 extend from the surface 34 of the tissue 40 (FIG. 1). The lower end 90 of each spring 84 is fastened to the outer surface 46, 92 of a corresponding guide plate 42, 44 near the bottom of the leading member 22.

The springs 84 are configured to continuously urge the first and second guide plates 42, 44 together so that in the absence of a force counteracting the springs, the outer passages 78 and central passage 82 remain substantially intact so that sutures are unable to pass laterally out of those passages.

The upper end 87 of the positioning member 88 carries grips 95, which may be in the form of two spaced apart annuli (FIG. 4). The grips 95 are sized to permit a surgeon to manipulate the positioning member 88 so that the knotting instrument 20 can be precisely directed to the location where the double knot is to be formed.

The trailing member 24 of the knotting instrument 20 is generally a flat, unitary member, preferably slightly thinner (as measured from left to right in FIG. 6) than the leading member 22. The bottom 96 of the trailing member is formed with a transverse groove 98 extending from one side to the other. Moreover, the outer bottom edges 100 of the trailing member are beveled at an angle corresponding to the angle defined by the sides of the V-shaped transverse groove 94 that is formed in the top 56 of the leading member 22. Accordingly, as best shown in FIG. 6, the beveled edges 100 of the trailing member bottom 96 bear upon the sides of the V-shaped groove 94 as the trailing member 24 is moved against the leading member 22.

Each vertical side 102 of the trailing member 24 has a guide groove 104 formed therein. Each guide groove 104 extends upwardly from a junction with the end of the transverse groove 98 in the trailing member bottom 96 to the top 106 of the trailing member 24. Preferably, a retainer bar 108 extends across each guide groove 104 at a location between the top 106 and bottom 96 of the trailing member 24. The retainer bars 108 prevent sutures from moving out of the guide grooves 104 in the trailing member 24.

The trailing member 24 is moved along the same path as the leading member 22. In the preferred embodiment, movement of the trailing member 24 is accomplished with a rod 110 that is attached to the top 106 of the trailing member 24. Preferably, the rod 110 is sized to pass through the central opening of the tubular positioning member 88 so that the longitudinal axis of the rod 110 is coaxial with the longitudinal axis of the positioning member 88.

The upper end of the rod 110 terminates in an annular grip 112 that is sized to receive the finger or thumb of the surgeon. As best shown in FIG. 4, the grips 95 of the positioning member 88 and the grip 112 on the end of rod 110 are configured to permit the surgeon to grasp the positioning member 88 while pushing the rod 110 to move the trailing member 24 relative to the leading member 22. Of course, the positioning member 88 and rod 110 may be moved so that the leading member 22 and trailing member 24 move simultaneously.

The following describes a preferred application of the knotting instrument 20 formed in accordance with this invention. Near the conclusion of a surgical procedure, the ends of two sutures 30, 32 (or, the opposite ends of a single suture) extend from tissue 40 inside a joint through an incision (not shown). The surgeon ties the free ends 35, 37 of the sutures 30, 32 into a single first knot 26. The suture segments 30A, 32A that extend from the first knot 26 are each passed through an outer passage 78 in the closed leading member 22.

A second knot 28 is tied in the suture segments 30A, 32A that extend from the top of the outer passages 78 in the leading member 22. The suture segments 30B, 32B that extend from the second knot 28 are then threaded through the guide grooves 104 in the trailing member 24. The portions of the suture segments 30B, 32B that extend from the top of the guide grooves 104 in the trailing member 24 are grasped by the surgeon, and the knotting instrument 20 is passed through the incision.

It is noteworthy that the distance ("D" in FIG. 5) between the two outer passages 78 in the leading member 22 and between the two guide grooves 104 in the trailing member 24 is sufficient to permit the knots 26, 28 to slide along the sutures 30, 32 (instead of tightening) as the knots 26, 28 are pushed toward the tissue surface 34 while the free ends 35, 37 of the sutures are held by the surgeon. The sufficient minimum distance D to ensure such sliding of the knots 26, 28 will vary with the characteristics (diameter, friction coefficients, etc.) of the sutures used. In a preferred embodiment, the distance D should be greater than or equal to the length ("d" in FIG. 5) of the knot, the knot length d being measured when the knot 26, 28 is next to the leading member 22 or trailing member as shown in FIG. 5. Preferably, the corners 79 (FIG. 3) in the outer passages 78 and the corners 105 (FIG. 5) in the guide grooves 104 over which sutures slide are rounded to prevent abrasion of the sutures.

As the knotting instrument 20 is moved toward the tissue surface 34, the knots 26, 28 continue to slide along the sutures 30, 32 until the first knot 26 bears upon the surface 34 of the tissue 40 at the location where the double knot is to be formed. Preferably, the leading member 22 and trailing member 24 are moved simultaneously toward the tissue surface 34. It is contemplated, however, that the leading member 22 may be moved independently, with the trailing member 24 later moved to slide the second knot 28 against the first knot 26. Irrespective of the technique employed for moving the knots, a primary advantage of the present invention is that the second knot 28 will ultimately be moved against the first knot 26 while the first knot 26 is held at the tissue surface 34 to form a tight double knot with substantial tension present in the portions of the sutures 30, 32 that extend between the tissue surface 34 and the double knot.

Figure 9:
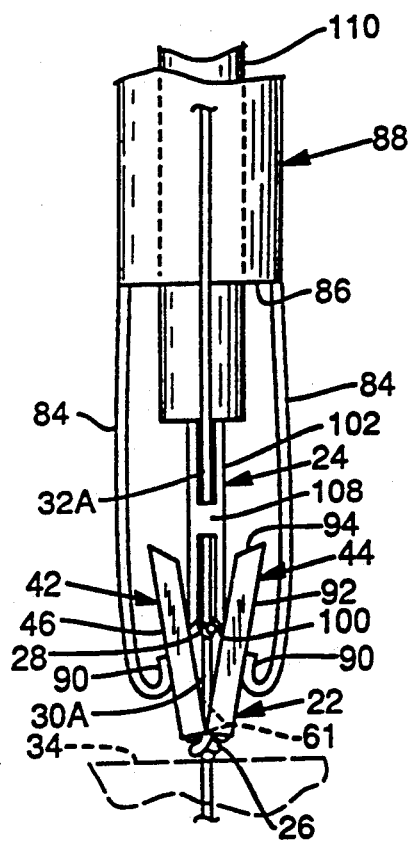
FIG. 9 is an enlarged detail view of the knotting instrument depicting movement of one knot toward another knot that is held at the surface of tissue.

More particularly, as best shown in FIGS. 6 and 9, the positioning member 88 and sutures are manipulated so that the first knot 26 is firmly held between the tissue surface 34 and the underside of the finger 60. The knot 26 fits within the guide space 68 that defined by the ridges 66 in the finger 60. As the surgeon pushes the rod 110, the beveled bottom 96 of the trailing member 24 forces apart the tops of the first and second guide plates 42, 44 against the bias of the springs 84. Accordingly, the second knot 28, which rests in the transverse groove 98 formed in the trailing member 24, is moved between those guide plates 42, 44 as the first knot 26 is prevented by the finger 60 from moving away from the tissue surface 34.

Continued downward pressure on the trailing member 24 (while the exposed free ends 35, 37 of the sutures are held by the surgeon) forces the second knot 28 to slide downwardly along the inclined upper edge 64 of the finger 60 until the second knot 28 meets the first knot 26 at the tip 61 of the finger. The surgeon then pulls the free ends 35, 37 of the sutures to tighten the second knot 28 against the first knot 26 while the trailing member 24 is pressed against both knots on the tissue surface 34.

The knots 26, 28 can be tightened together when the second knot 28 is against the first knot 26 because the suture segments 30A, 32A between the knots slide out of the outer grooves 50, 80 in the parted guide plates 42, 44 and toward each other as the second knot 28 slides to the tip 61 of the finger 60. Put another way, the above-mentioned distance D between those suture segments 30A, 32A substantially decreases as the second knot 28 is moved against the first knot 26.

With the knots 26, 28 tightened, the knotting instrument 20 is withdrawn from the joint through the incision. Withdrawal of the leading member 22 is facilitated by the provision of the central passage 82 extending through the leading member 22. More particularly, central passage 82 provides clearance for the portions of the sutures 30, 32 (see dashed lines in FIG. 5) that slide toward the center of the leading member 22 as the trailing member 24 is withdrawn from between the guide plates 42, 44. It can be appreciated that in the absence of the central passage 82, the spring-biased first and second guide plates 42, 44 would clamp the sutures 30, 32 as the trailing member is withdrawn from between those guide plates.

While the present invention has been described in relation to a preferred embodiment, it is to be understood that various alterations, substitutions of equivalents and other changes can be made without departing from the spirit and scope of the invention as described in the claims.

What is claimed is:

1. A knotting instrument comprising:
   a leading member having grooves therein through which fit segments of sutures that extend from a first knot in a suture;
   a trailing member movable relative to the leading member and having grooves formed therein for receiving portions of the segments that extend through the grooves in the leading member, the trailing member having a bottom part shaped to slide a second knot in the suture segments toward the first knot as the trailing member is moved relative to the leading member; and
   a finger member connected to the leading member and having protruding portions formed thereon to define a space shaped for holding the first knot against the finger as the trailing member is moved to slide the second knot along the finger toward the first knot.

2. The instrument of claim 1 wherein the leading member and the trailing member are shaped so that the segments in the leading member grooves are forced out of the leading member grooves as the trailing member is moved to slide the second knot toward the first knot.

3. A method for moving knots in sutures to a selected location, comprising the steps of:

securing within a pair of spaced apart grooves suture segments that extend from a first knot in the sutures;

sliding the first knot along the sutures to move the knot to a selected location;

holding with a finger mechanism the first knot at the selected location;

sliding a second knot in the sutures along the finger mechanism toward the held first knot so that the suture segments slide out of the grooves while the first knot is held by the finger mechanism as the second knot is slid toward the first knot.

* * * * *